United States Patent
Schaap et al.

(10) Patent No.: US 10,041,097 B2
(45) Date of Patent: Aug. 7, 2018

(54) DEAERATION PROCESS

(75) Inventors: Albert Schaap, Barendrecht (NL); Daniel Verkoeijen, The Hague (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/333,252

(22) Filed: Dec. 21, 2011

(65) Prior Publication Data

US 2012/0095246 A1 Apr. 19, 2012

Related U.S. Application Data

(63) Continuation of application No. 12/874,648, filed on Sep. 2, 2010, which is a continuation of application No. 10/583,890, filed as application No. PCT/EP2004/014884 on Dec. 28, 2004, now abandoned.

(30) Foreign Application Priority Data

Dec. 30, 2003 (EP) ..................................... 03258249

(51) Int. Cl.
*C11B 1/10* (2006.01)
*C07C 57/03* (2006.01)
*C12P 7/64* (2006.01)

(52) U.S. Cl.
CPC .............. *C12P 7/6472* (2013.01); *C11B 1/10* (2013.01); *C12P 7/6427* (2013.01); *C12P 7/6463* (2013.01)

(58) Field of Classification Search
CPC .................................. C11B 1/10; C07C 57/03
USPC .................................................. 554/175, 224
See application file for complete search history.

(56) References Cited

U.S. PATENT DOCUMENTS

| | | | |
|---|---|---|---|
| 3,082,228 A | 3/1963 | Sutherland | |
| 4,575,117 A | 3/1986 | Vollmer et al. | |
| 4,789,554 A | 12/1988 | Scavone et al. | |
| 4,970,167 A | 11/1990 | Baugh et al. | |
| 5,658,767 A * | 8/1997 | Kyle ..................... | A23C 11/04 426/585 |

FOREIGN PATENT DOCUMENTS

| | | |
|---|---|---|
| EP | 1065196 | 1/2001 |
| WO | WO1989011521 | 11/1989 |
| WO | WO 97/37032 | 9/1997 |
| WO | WO 97/37032 | 10/1997 |
| WO | WO200073254 | 12/2000 |
| WO | WO2001051598 A1 | 7/2001 |
| WO | WO2001054510 A1 | 8/2001 |
| WO | WO2003092628 A2 | 11/2003 |
| WO | WO2005063999 A1 | 7/2005 |
| WO | WO2006079533 | 8/2006 |

OTHER PUBLICATIONS

International Search Report for PCT/EP2004/014884 dated Apr. 5, 2005.
Napier, Trends in Plant Science, Plumbing the depths of PUFA biosynthesis: a novel polyketide synthase-line pathway from marine organisms, 2002, 51-54, 7.
Yamamura et al, AOCS Press, Industrial high-performance liquid chromatography purification of docosahexaenoic acid ethyl ester . . . , 1997, 1435-1440, 74.
Young, Fish Oil Bulletin, The chemical & physical properties of crude fish oils for refiners & hydrogenerators, 1986, 1-18, 18.

\* cited by examiner

*Primary Examiner* — Hamid R Badr
(74) *Attorney, Agent, or Firm* — Shannon McGarrah; Xi Chen

(57) ABSTRACT

A process for producing an oil, or a polyunsaturated fatty acid (PUFA), is described where an aqueous liquid comprising cells is deaerated, and the oil or PUFA is obtained from the cells. Deaeration can be performed by a wide variety of techniques, including the application of a vacuum (or reduced pressure), mechanical deaeration or degassing by reduced stirring or subjecting the broth to centrifugal forces, reducing viscosity (by dilution or heating), reduction in the supply of oxygen or air during fermentation or a reduction in stirring rate, lowering the pH (to lower the solubility of $CO_2$), filtration using PTFE capillaries, gas displacement (by bubbling in nitrogen or helium) or chemical deaeration (using oxygen scavengers).

16 Claims, No Drawings

DEAERATION PROCESS

CROSS-REFERENCE

This application is a continuation of commonly owned U.S. application Ser. No. 12/874,648, filed Sep. 2, 2010, which is a continuation of U.S. Ser. No. 10/583,890, filed Jun. 22, 2006 (now abandoned), which in turn is the national phase application under 35 USC § 371 of PCT/EP2004/014884, filed Dec. 28, 2004 which designated the U.S. and claims priority to EP 03258249.6, filed Dec. 30, 2003, the entire contents of each of which are hereby incorporated by reference.

FIELD OF THE INVENTION

The present invention relates to a process for producing an oil, or an polyunsaturated fatty acid (PUFA). The process involves deaerating an aqueous liquid comprising cells from which the oil or PUFA is (later) obtained. After deaeration, the cells may be pasteurised. The oil or PUFA may then be extracted, purified or isolated from the cells.

BACKGROUND OF THE INVENTION

Polyunsaturated fatty acids, or PUFAs, are found naturally and a wide variety of different PUFAs are produced by different single cell organisms (algae, fungi, etc). One particularly important PUFA is arachidonic acid (ARA) which is one of a number of Long Chain Poly-Unsaturated Fatty Acids (LC-PUFAs). Chemically, arachidonic acid is cis-5,8,11,14 eicosatetraenoic acid (20:4) and belongs to the (n-6) family of LC-PUFAs.

Arachidonic acid is a major precursor of a wide variety of biologically active compounds, known collectively as eicosanoids, a group comprising prostaglandins, thromboxanes and leukotrienes. Arachidonic acid is also one of the components of the lipid fraction of human breast milk and is thought to be essential for optimal neurological development in infants. Arachidonic acid has a wide variety of different applications including use in infant formula, foodstuffs and animal feeds.

WO-A-97/37032 refers to the preparation of a microbial PUFA-containing oil from pasteurised biomass. However, there is no disclosure of deaeration prior to pasteurisation.

WO-A-04/001021 published on 31 Dec. 2003 describes more detailed pasteurisation conditions.

Processes involving heating biomass, or microbial cells, are known. WO-A-97/37032 describes that microbial cells can be pasteurised prior to extraction to a PUFA therefrom in the form of an oil. However, the present applicants have found that inclusion of a deaeration process can improve the quality of the oil that can be extracted from the cells. In particular, the resulting oil may oxidise less, or be less oxidised, and may have a lower peroxide value (POV) and/or anisidine value (AnV).

DESCRIPTION OF THE INVENTION

The present invention therefore provides an improved process for producing an oil, or a polyunsaturated fatty acid (PUFA). The improvement is the use of deaeration preferably prior to pasteurisation.

A first aspect of the present invention therefore relates to a process for producing an oil, or a polyunsaturated fatty acid (PUFA), the process comprising:

a) deaerating an aqueous liquid comprising cells; and
b) obtaining the oil or PUFA from the cells.

The aqueous liquid is preferably a broth or culture medium, such as a fermentation broth or a broth resulting from fermentation. It may be a liquid taken or removed during fermentation, although preferably it is a broth at the end of fermentation. The cells are preferably microbial cells. The microbial cells may be alive prior to, during and/or after deaeration.

The deaeration of the aqueous liquid preferably results in the removal of air, such as entrained, entrapped, undissolved and/or dissolved air. The process may therefore effectively be, or comprise, a degassing. It may remove gas (e.g. air bubbles). Preferably, the process will remove oxygen, such as dissolved oxygen (e.g. in an entrapped form, or as bubbles). In this context "dissolved" refers to the gas, such as air or oxygen, being present or dissolved in the aqueous liquid (rather than any gas inside the cells).

The deaeration process may also result in other gases being removed from the aqueous liquid, for example carbon dioxide.

The deaeration, because it can preferably remove at least part of the dissolved and/or some undissolved oxygen, can result in reduced oxidation. This may mean that the PUFA and/or the oil may be less oxidised, and therefore of better quality.

It is not immediately apparent that removal of oxygen would be advantageous, because of course the microbial cells require oxygen in order to be able to survive and grow. Indeed, in many fermentation processes, including the preferred processes of the invention, air is supplied to the microbial cells, for example supplied to (such as bubbled into) the aqueous liquid, or culture medium. The cells will divide and grow, and preferably in so doing will also biosynthesise one or more PUFAs. The idea then of stopping oxygen or air supply during the fermentation process in order to effect deaeration, would not be necessarily thought to be an advantageous strategy because this might result in the cells dying, or at the very least their ability to produce PUFAs and other valuable compounds might be compromised.

Deaeration is known for foodstuffs, such as milk, and orange juice, and also in some industrial processes, such as in the manufacture of paper. However, it will be realised that these processes are in a different field from the fermentation of microbial organisms, in particular in order to produce a compound to be extracted, and in those (prior art) systems there are no (living) cells. In some prior art processes, deaeration is performed to reduce bacterial growth, whereas in the present invention, microbial cell growth and survival (including bacterial cells), in order to produce PUFAs, is an important element of the fermentation process that requires oxygen.

There are a number of ways of performing deaeration, including the following:— a) application of vacuum (or reduced pressure);
b) mechanical deaeration/de-gassing (stirring, vibration, use of accelerative forces, e.g. g-force, such as in a centrifuge or a cyclone);
c) viscosity changes (either by dilution with water or other liquids, or by temperature change);
d) change in fermentation conditions, for example a reduction in airlift, air sparging, or the supply of oxygen or air during fermentation, or a reduction in stirring rate;
e) pH change, for example by lowering pH or acidification (e.g. by using carbon dioxide, which when it dissolves in the liquid it forms carbonic acid);

f) filtration, for example by using a filter, capillary or membrane, such as a (preferably inert) polymer, for example PTFE;

g) gas displacement, with an inert gas such as nitrogen or a noble gas such as helium;

h) chemical deaeration, for example using an oxygen scavenger, for example sodium sulphite or hydrazine;

i) time, such as allowing the aqueous liquid to rest, or under conditions that allow a gas such as oxygen or air to diffuse out of the liquid; and/or j) a combination of one or more of the above methods.

Each of the above nine deaeration methods will now be discussed in more detail.

1. Vacuum (or Reduced Pressure)

A vacuum can be applied above the surface of the aqueous liquid. However, a true vacuum need not always be necessary, instead a preferred method involves a reduction of pressure above the surface of the aqueous liquid, for example while it is in a vessel, such as a fermenting vessel. Preferably the pressure above the aqueous liquid is less than atmospheric or room pressure, or at least represents a reduction in pressure when compared with the pressure inside the fermentor vessel (or pressure during fermentation). There may be thus a pressure reduction when deaeration is to begin, for example once fermentation has finished.

The vacuum or reduced pressure may be applied in a separate vessel from the one in which fermentation took place (such as the fermentor). Liquid may therefore be transferred to a vacuum workstation, or a separate container where a vacuum is applied or can be present. In this context, when discussing the application of a "vacuum" as one of the methods of deaeration, this should be understood as the application of reduced pressure to the aqueous liquid. This is because it is not absolutely essential that a total vacuum be applied.

Preferably, the pressure applied (during the vacuum deaeration stage) is no more than 800, preferably no more than 600, and optimally no more than 400 mbara (millibar pressure absolute). Under certain circumstances, using the correct equipment, the pressure is preferably no more than 200 or 100 mbara. Preferably the reduced pressure is from 50 to 600 mbara, such as 100 to 500 mbara, and optimally from 200 to 450 mbara.

In a preferred embodiment the aqueous liquid, such as after fermentation, is transferred to a vessel having a reduced pressure, in other words a pressure less than the fermentor (or other vessel from which the aqueous liquid is being transferred). The transfer of the aqueous liquid from these two vessels (such as from a fermentor to reduced pressure vessel) may be assisted, or caused by, that difference in pressure. There may therefore be a transfer pressure, representing the pressure that the aqueous liquid is subjected to during movement from one vessel to the other. This transfer pressure is preferably no more than 0.7, such as 0.6, and preferably no more than 0.5 bar. The transfer pressure may be between 0.7 and 0.3 bar, such as from 0.6 to 0.4 bar.

The reduced pressure vessel may have means for increasing the surface area of the aqueous liquid, to assist deaeration. Thus the aqueous liquid may take on the form of a film, such as a thin film. The aqueous liquid may be forced into a film (such as a thin film) by a mechanical device, for example a nozzle, such as an umbrella nozzle, or a parasol deaerator. The aqueous liquid may therefore be forced onto a curved surface while reduced pressure is applied. By increasing the surface area of the aqueous liquid, such as by forming a film or a spray, this can assist deaeration process, and can result in more efficient degassing. The level of the aqueous liquid inside the reduced vacuum vessel (which will contain the nozzle or curved surface onto which the aqueous liquid is forced) may be from 1 to 2 tenths full. The then deaerated aqueous liquid may then be transferred to a pasteurisation or heating vessel or workstation.

2. Mechanical Deaeration

Often during fermentation, oxygen or (more usually) air is supplied to the aqueous liquid (culture medium or fermentation broth). This is to allow the microbial cells to grow and divide and to biosynthesise PUFAs.

During fermentation the aqueous liquid may be stirred. In order to deaerate, the amount of stirring (or stirring rate) may be reduced or slowed, or stopped altogether. Reduced stirring is less likely to cause cavitation, such as on or near the stirring blade or moving surface(s), and is less likely to create bubbles (in the aqueous liquid).

Stopping stirring, or reducing the degree of stirring, may allow bubbles in the aqueous liquid to coalesce, and thereby rise towards the surface of the aqueous liquid. During this reduction of stirring, the stirring rate may be reduced to no more than one half, one third, or even a quarter, of that during fermentation. For example, if the stirring rate is 80 rpm, reduced stirring, to allow deaeration, may involve stirring at a rate no more than 40 rpm.

Mechanical deaeration may also involve reduction in the amount of air or oxygen supplied to the aqueous liquid (fermentation broth, by means of aeration). The rate of air or oxygen addition may be slowed, or stopped altogether. During deaeration the rate of air (or oxygen) supply may be reduced to no more than a half, a third, or even a quarter (such as of the rate during fermentation). Thus aeration of the liquid may stop or cease before the and of fermentation (e.g. for up to 5, 2 or 1 hours).

Often air (or oxygen) is supplied to the aqueous liquid during fermentation, and while it is in the fermentation vessel (or fermentor). The gas is allowed to bubble into the aqueous liquid and this may be by means of a sparger. Deaeration may involve reduction of the rate of air or oxygen supply by means of the sparger.

Deaeration may also be achieved by vibration where the aqueous liquid is passed through or into a (static) vibration vessel, such as a tube.

The aqueous liquid maybe deaerated by using a degassing pump. The aqueous liquid may be subjected to accelerative forces, for example in a cyclon. The liquid may therefore be subjected to centrifugal force which may assist in the deaeration. The cyclone may rapidly rotate the aqueous liquid, and subject it to centrifugal force, in a vessel whereby the gases that escape from the liquid may rise, and may be taken out or removed from the top of the cyclone, while the liquid that has been deaerated may flow in the opposite direction (such as downwardly).

A mechanical vacuum deaerator may be employed to deaerate the aqueous liquid. This may be a pump to which a vacuum (or reduced pressure) can be applied. Modified (e.g. centrifugal) pumps, that can accept reduced pressure, or can generate a vacuum, are commercially available. Preferably the vacuum pump will have a rotating chamber, where gas bubbles can be removed from the aqueous liquid, for example under the action of centrifugal force.

Alternative types of equipment include degassing pumps. This may be able to effect degassing of gas-dissolved liquids. The pump may have a (e.g. interlocked) vacuum pump. It may be able to perform degassing without any chemical additives. Such systems may be able to degas to a level of 0.5 ppm or less. They may be able to have a flow rate of 25 liters/minute or less. Suitable degassing pumps are available from the Yokota Manufacturing Company in Japan.

3. Viscosity Adjustment

An increase in viscosity can be achieved by heating the aqueous liquid. This heating can also result in deaeration.

A reduction in viscosity may allow gasses in the aqueous liquid to surface more efficiently. Thus, methods of reducing the viscosity can assist in the deaeration process. This can be achieved by adding another liquid (itself deaerated, or with a lower air/oxygen content than the aqueous liquid), such as water, and so the process may comprise dilution. The aqueous liquid is often quite viscous due to the presence of cells and nitrogen and/or carbon sources for assimilation by cells.

Another method of reducing viscosity is by heating the aqueous liquid. An increase in temperature decreases the solubility of oxygen in the liquid.

4. pH Adjustment

The aqueous liquid can be made more acidic. This can lower the solubility of air/oxygen therein.

It will be realised that the aqueous liquid comprises live cells that can synthesise valuable compounds. The cells "breathe" in the sense that they consume oxygen, and liberate carbon dioxide. The carbon dioxide may dissolve in the aqueous liquid, and in so doing produces carbonic acid. By lowering the pH, this can make the aqueous liquid more acidic, and so reduce the solubility of carbon dioxide (or oxygen) in it.

5. Filtration

The aqueous liquid may be passed through a filter or membrane which may be able to remove small bubbles, such as of air. This can be performed on a relatively small scale. A filter or membrane preferably comprises an inert material, such as a polymer. The material (e.g.) polymer may comprise a halogen alkylene, such as PTFE.

The aqueous liquid may therefore be passed through (e.g. a small, or relatively fine) tube or capillary. This may comprise (e.g. in a wall) or have (a coating of) a polymer, such as PTFE. The tube may have holes or apertures through which dissolved gasses or bubbles may pass. The aqueous liquid may be passed through these tubes or capillaries under pressure.

6. Gas Displacement

This involves displacing or replacing oxygen or air (dissolved or otherwise) in the aqueous liquid. Air or oxygen can be replaced by many a wide range of gases, as long as, preferably, dissolved oxygen is forced out of solution, and can than leave the aqueous liquid. An inert gas is preferred, for example nitrogen, or a noble gas, such as helium. The gas may be provided above, on top of, the aqueous liquid (such as in the headspace of the fermentor). For example, it may be added or supplied to the headspace above the liquid, for example in a vessel such as a fermentor. Alternatively, the gas can be supplied to the aqueous liquid, for example by bubbling in, or by use of the sparger. The preferred gas is nitrogen, although a gas comprising nitrogen (but with a reduced amount of oxygen, such as below 20% or below 10% or 15%, so it is below atmospheric levels) may be employed.

The preferred technique is to reduce, or stop, the amount of air (or oxygen) supplied to the aqueous liquid before ending fermentation. First, for example, no air may be supplied, e.g. via a sparger, for at least one or two hours prior to the end of fermentation. Instead of supplying air via the sparger, one can supply a gas other than air or oxygen, for example one with a reduced oxygen content, for example nitrogen. Thus, preferably, one can supply nitrogen to the aqueous liquid up to one or two hours prior to the end of fermentation. This may create an inert or reduced oxygen content (e.g. nitrogen rich) atmosphere above the aqueous liquid, for example an atmosphere that has a higher content of nitrogen than atmospheric air. The pressure of nitrogen above the aqueous liquid may be from 0.4 to 0.8 bar, such as about 0.6 bar.

7. Chemical Deaeration

This can be achieved by using a substance or chemical that can advantageously react with air, or more importantly the oxygen in the air. The substance may be an oxygen scavenger. This substance may be brought into contact with the aqueous liquid. The chemical may be added to the aqueous liquid, for example while it is in a vessel, such as a fermentor vessel. Suitable oxygen reacting materials, including oxygen scavengers, are well known in the art, and include alkali metal (such as sodium) sulphite and compounds comprising hydrazine. Other (non-chemical) deaeration method(s) may be used if the PUFA or oil is to be used in a foodstuff.

8. Time

If left to rest, the aqueous liquid will slowly give up its dissolved gases, such as oxygen and air. Dissolved gases may diffuse out of the aqueous liquid. Thus the gases may gradually, over time, come out of solution.

Measurement of Air/Oxygen Content

This can be achieved by using standard techniques in the art. For example, one can use an EGT (entrained gas tester). The amount of air can be measured by online techniques in the aqueous liquid (effectively a microbial suspension of the cells).

The entrained gas (gas bubbles) can be measured by compressing a sample in a measuring cell. The volumetric share of the entrained gas is calculated then by Boyle's Law (pV=constant). On the other hand, the dissolved gas that may be released can be measured by expanding the sample. This simulates a sharp drop in the pressure. As the pressure in the measuring cell is reduced, the solubility of gases decreases, and are released. Thus the volume of the suspension increases. The operation can be fully automatic and/or may comprise an on-line gas analyzer, at an appropriate place in the system, suitably after deaeration.

Deaeration may result in an $O_2$ content (in the aqueous liquid) of less than 20 or 15 ppm, for example from 2 or 5 to 15 or 20 ppm. The concentration of the (e.g. dissolved) oxygen may be preferably less than 10, such as less than 5, and optimally less than 2 ppm.

Preferably, deaeration takes place so that the concentration of (dissolved) oxygen is less than 0.03 cc/liter (44 ppb), preferably less than 0.005 cc/liter (7 ppb).

The deaerated aqueous liquid (obtained by deaerating the aqueous liquid comprising the cells according to the invention) may advantageously be subjected to increased pressure and/or increased temperature. Increased pressure and/or increased temperature may for instance be present during heating and/or pasteurising of the cells.

In a preferred embodiment, the process according to the invention comprises subjecting the deaerated aqueous liquid to a pressure of at least 1 bara, preferably at least 1.5 bara, preferably at least 2 bara, preferably at least 5 bara. There is no specific upper limit for the pressure. The deaerated aqueous liquid may for instance be subjected to a pressure below 40 bara, for instance below 20 bara.

In a preferred embodiment, the process according to the invention comprises subjecting the deaerated aqueous liquid to a temperature of at least 60° C., preferably at least 80° C., preferably of at least 90° C., preferably of at least 100° C., preferably at least 110° C. There is no specific upper limit for the temperature. The deaerated aqueous liquid may for instance be subjected to a temperature below 150° C.

Preferably, the deaerated aqueous liquid that may be subjected to the increased temperature and/or increased pressure has the preferred $O_2$ content and/or preferred concentration of (dissolved) oxygen as disclosed herein.

Pasteurisation Process

Pasteurisation will usually take place after deaeration and/or fermentation has finished. In a preferred embodiment, pasteurisation will finish the fermentation, because the heat during pasteurisation will kill the cells. Pasteurisation may therefore be performed on the fermentation broth (or the cells in the liquid (aqueous) medium), although it can be performed on the microbial biomass obtained from the broth. In the former case, pasteurisation can take place while the microbial cells are still inside the fermenter. Pasteurisation preferably takes place before any further processing of the microbial cells, for example granulation (e.g. by extrusion) crumbling, or kneading.

Once fermentation has been finished, the fermentation broth may be filtered, or otherwise treated to remove water or aqueous liquid. After water removal, one may obtain a biomass "cake". If pasteurisation has not taken place, then the dewatered cells (or biomass cake) can be subjected to pasteurisation.

Pasteurisation can be performed by heating (the cells) directly or indirectly. The heating, if direct, may be by passing steam into the fermenter. An indirect method may use a medium via heat exchangers, either through the wall of the fermenter, or with heating coils, or an external heat exchanger such as a plate heat exchanger.

Usually, pasteurisation will take place in the fermenter vessel in which fermentation has occurred. However, for some organisms (such as bacteria) it is often preferred to remove the cells from the vessel first, and than pasteurise. Pasteurisation may take place before other processing of the organisms, for example drying or granulation.

Pasteurisation will usually kill most, or if not all, of the micro-organisms. Following pasteurisation, at least 95%, 96% or even 98% of the micro-organisms may have been killed, that is to say they are not alive.

Heating or pasteurisation of the cells may be effected at any suitable temperature, preferably at a temperature of least 60° C., preferably at least 80° C., preferably at least 90° C., preferably at least 100° C., preferably at least 110° C. There is no specific upper limit for the temperature. The pasteurisation may for instance be effected at a temperature below 150° C. Preferred pasteurisation processes are described in WO 97/37032 and WO-A-04/001021.

Extraction of a PUFA

The present invention may involve extracting and/or isolating a PUFA from the (e.g. pasteurised) cells. Preferably this is after deaeration and (optionally) also after pasteurisation.

The extraction may first start with the addition of an alkali earth metal halide, such as calcium chloride. The cells may (then) be subjected to filtration, washing and/or squeezing, in order to generate a wet cake.

The microbial cells can then be subjected to extrusion, and if necessary the resulting extruded granules or extrudate, subjected to drying. The resulting dried granules, or dried biomass, can then used to extract one of the PUFAs, preferably an oil containing one or more PUFAs. Preferred extraction processes for preparing an oil containing a PUFA from microbial cells are described in International Patent Application Nos. PCT/EP99/01446 (WO 97/36996), PCT/EP97/01448 (WO 97/37032) and PCT/EP01/08903 (WO 02/10423).

Polyunsaturated Fatty Acids (PUFAs) and Microbial Oils

The PUFA can either be a single PUFA or two or more different PUFAs. The or each PUFA can be of the n-3 or n-6 family. Preferably it is a C18, C20 or C22 PUFA. It may be a PUFA with at least 18 carbon atoms and/or at least 3 or 4 double bonds. The PUFA can be provided in the form of a free fatty acid, a salt, as a fatty acid ester (e.g. methyl or ethyl ester), as a phospholipid and/or in the form of a mono-, di- or triglyceride.

Suitable (n-3 and n-6) PUFAs include:
docosahexaenoic acid (DHA, 22:6 Ω3), suitably from algae or fungi, such as the (dinoflagellate) *Cryptheco-dinium* or the (fungus) *Thraustochytrium*;
γ-linolenic acid (GLA, 18:3 Ω6);
α-linolenic acid (ALA, 18:3 Ω3);
conjugated linoleic acid (octadecadienoic acid, CLA);
dihomo-γ-linolenic acid (DGLA, 20:3 Ω6);
arachidonic acid (ARA, 20:4 Ω6); and
eicosapentaenoic acid (EPA, 20:5 Ω3).

Preferred PUFAs include arachidonic acid (ARA), docosohexaenoic acid (DHA), eicosapentaenoic acid (EPA) and/or γ-linolenic acid (GLA). In particular, ARA is preferred.

The PUFA may be produced by the cells pasteurised in the process of the invention, such as a microbial cell. This may be a bacteria, algae, fungus or yeast cell. Fungi are preferred, preferably of the order Mucorales, for example *Mortierella, Phycomyces, Blakeslea, Aspergillus, Thraustochytrium, Pythium* or *Entomophthora*. The preferred source of ARA is from *Mortierella alpina, Blakeslea trispora, Aspergillus terreus* or *Pythium insidiosum*. Algae can be dinoflagellate and/or include *Porphyridium, Nitszchia*, or *Cryptheco-dinium* (e.g. *Crypthecodinium cohnii*). Yeasts include those of the genus *Pichia* or *Saccharomyces*, such as *Pichia ciferii*. Bacteria can be of the genus *Propionibacterium*. The microbial oil may be a liquid (at room temperature).

It is preferred that most of the PUFA is in the form of triglycerides. Thus, preferably at least 50%, such as at least 60%, or optimally at least 70%, of the PUFA is in triglyceride form. However, the amount of triglycerides may be higher, such as at least 85%, preferably at least 90%, optimally at least 93% or 95% of the oil. Of these triglycerides, preferably at least 40%, such as at least 50%, and optimally at least 60% of the PUFA is present at the a-position of the glycerol (present in the triglyceride backbone), also known at the 1 or 3 position. It is preferred that at least 20%, such as at least 30%, optimally at least 40% of the PUFA is at the b(2) position.

The microbial oil may comprise at least 10, 35, 40 or 45% or more of a desired PUFA, such as arachidonic acid. It can have triglyceride content of at least 90%, such as from 92-94%. Typically, the microbial oil will have an eicosapentaenoic acid (EPA) content of below 5%, preferably below 1% and more preferably below 0.5%. The oil may have less than 5%, less than 2%, less than 1% of each of $C_{20}$, $C_{20:3}$, $C_{22:0}$ and/or $C_{24:0}$ fatty acids. The free fatty acid (FFA) content may be no more than 1.0, 0.4, 0.2 or 0.1. The oil may have little or no GLA and/or DGLA.

The microbial oil may be a crude oil. It may have been extracted from the cells by using a solvent, such as an organic liquid, such as hexane or isopropanol.

PUFA Extraction Process

The PUFA (or microbial oil, usually comprising the PUFA) may then be extracted from the (pasteurised) microbial cells. Preferably, it is extracted from (e.g. dried) granules (e.g. extrudates) containing the cells. The extraction can be performed using a solvent. Preferably a non-polar solvent is used, for example a $C_{1-8}$, preferably $C_{2-6}$, alkane, for example hexane.

Preferably, the solvent is allowed to percolate over the dried granules. Suitable micro-organism granulation and extrusion techniques and subsequent extraction of a microbial PUFA containing oil, are described in WO-A-97/37032.

The solvent allows one to obtain a crude PUFA containing oil. This oil can be used in that state, without further processing, or it can be subjected to one or more refining steps. However, a crude oil is usually one that contains a solvent, such as a solvent used to extract the oil (e.g. hexane, or an alcohol such as isopropyl alcohol) or that has not been subjected to one (or preferably all) of the following refining step. Suitable refining protocols are described in International patent application no. PCT/EP01/08902 (the contents of this document and all others described herein are hereby incorporated by reference). For example, the oil can be subjected to one or more refining steps which can include acid treatment or degumming, alkali treatment or free fatty acid removal, bleaching or pigment removal, filtration, winterisation (or cooling, for example to remove saturated triglycerides), deodorising (or removal of free fatty acids) and/or polishing (or removal of oil-insoluble substances). All these refining steps are described in greater detail in PCT/EP01/08902 and can be applied to the steps described in the present application mutatis mutandis.

The resulting oil is particularly suitable for nutritional purposes, and can be added to (human) foods or (animal) feedstuffs. Examples include milk, infant formula, health drinks, bread and animal feed.

Cells

The cells may be any cells from which an oil or a PUFA can be obtained. Preferably, the cells are microbial cells. The microbial cells (or micro-organisms) used in the present invention can be any of those described earlier especially in the section concerning PUFAs and microbial oils. They may comprise, or be able to produce, a PUFA or microbial oil, and suitably the PUFA oil may be extracted or isolated from the cells. They may be in filamentous form, like fungi or bacteria, or single cells like yeast, algae and bacteria. The cells may comprise micro-organisms that are yeast, fungi, bacteria or algae. Preferred fungi are of the order Mucorales for example, the fungus may be of the genus *Mortierella*, *Phycomyces*, *Blakeslea* or *Aspergillus*. Preferred fungi of the species *Mortierella alpina*, *Blakeslea trispora* and *Aspergillus terreus*.

As far as yeasts are concerned, these are preferably of the genus *Pichia* (such as of the species *Pichia ciferrii*) or *Saccharomyces*.

Bacteria can be of the genus *Propionibacterium*.

If the cells are from an algae, this is preferably a dinoflagellate and/or belongs to the genus *Ciypthecodinium* or *Daniella*. Preferred algae are of the species *Crypthecodinium cohnii* or *Daniella saline*.

Peroxide Value (POV)

Preferably the POV of the (microbial) oil is from 3 to 8 or 12. However, lower POV values can be obtained using the process of invention, and these values may be less than 10.0 or less than 8.0. The POV can be measured using techniques know in the art, for instance according to AOCS Cd-8-53. The unit (for POV) is usually meq/kg.

Anisidine Value (AnV)

This value can give a measure of the aldehyde content. Preferably the anisidine value of the (microbial) oil is from 5, 6, 7 or 10 to 15, 20 or 25. Suitably the AnV no more than 20, for example no more than 15. It may be no more than 10 or even no more than 5 or 2. AnV values (in preferred experiments) ranged from 5 to 15, optimally from 7 to 12. Preferably the AnV is from 2 or 5 to 12 or 15. The AnV can be measured using techniques known in the art, for instance according to AOCS Cd-18-90.

Uses of Oils and PUFAs

A further aspect of the invention relates to a composition comprising the oil and, where appropriate, or more (additional) substances. The composition may be a foodstuff and/or a food supplement for animals or humans. The oils may be rendered suitable for human consumption, if necessary, typically by refining or purification of the oil obtained from the microbes.

The composition may be an infant formula or (human) foodstuff. Here the composition of the formula may be adjusted so it has a similar amount of lipids or PUFAs to normal breast milk. This may involve blending the microbial oil of the invention with other oils in order to attain the appropriate composition.

The composition may be an animal or marine feed composition or supplement. Such feeds and supplements may be given to any farm animals, in particular sheep, cattle and poultry. In addition, the feeds or supplements may be given to farmed marine organisms such as fish and shell fish. The composition may thus include one or more feed substances or ingredients for such an animal.

The oil of the invention may be a crude or refined oil. It can be sold directly as oil and contained in appropriate packaging, typically one piece aluminium bottles internally coated with epoxy phenolic lacquer, and flushed with nitrogen. The oil may contain one or more antioxidants (e.g. tocopherol, vitamin E, palmitate) each for example at a concentration of from 50 to 800 ppm, such as 100 to 700 ppm.

Suitable compositions can include pharmaceutical or veterinary compositions, e.g. to be taken orally. or cosmetic compositions. The oil may be taken as such, or it may be encapsulated, for example in a shell, and may thus be in the form of capsules. The shell or capsules may comprise gelatine and/or glycerol. The composition may contain other ingredients, for example flavourings (e.g. lemon or lime flavour) or a pharmaceutically or veterinary acceptable carrier or excipient.

Defoamers

During deaeration bubbles of gas may form in the aqueous liquid. This may happen during the process of degassing, as gasses come out of solution and can rise (as bubbles) towards the surface of the aqueous liquid. As will be expected, this may cause a foam to form on the top of the aqueous liquid. Should a foam not be desired, one can reduce or prevent foam formation by the addition of one or more defoamers to the aqueous liquid. Such defoamers are known in the art, and then the appropriate defoamer may be deployed, for example tributyl phosphate. The defoamer preferably of a hydrophobic nature, and may be insoluble in water. It may comprise a non-polar hydrocarbon chain, for example modified by a polar group. Preferred defoamers include silicone oil, paraffin, fatty alcohol alkoxylate and/or a polyglycol.

Preferred chemical deaerators include aliphatic alcohols, fatty acid esters, fatty acid ethoxylates, fatty acid polyethers and/or fatty alcohols.

Deaeration may have further benefits, especially if the microbial cells are to be heated, for example they need to be killed or subjected to pasteurisation. The cells, or the aqueous liquid (or whatever composition comprises the cells at the appropriate stage) may be subjected to high temperatures and/or high pressures during heating or pasteurisation. This can cause gases to suddenly or violently leave the aqueous liquid, for example it may cause cavitation in pumps during microbial cell transfer. This is undesirable as it may cause cell wall disruption, in other words break open the cells. Therefore, a prior deaeration step may reduce possible problems that may arise during high temperatures or pressures, for example during heating or pasteurisation.

Equipment (e.g Industrial Process Plant)

A second aspect of the invention relates to apparatus suitable for conducting the process of the first aspect. The second aspect may thus comprise:

(a) means for culturing (or fermenting) microbial cells (e.g. a fermentor), optionally linked to;

(b) means for deaerating an aqueous liquid comprising the microbial cells; and (c) optionally, means for obtaining a (resulting) oil from the microbial cells.

In one embodiment the dearation in (b) may take place while the cells are (still) inside the fermentor. In an alternative the deaeration means may be separate (although optionally connected to) the deaeration means in (b). Thus the cells and culture medium (e.g. broth) may be passed or transferred (e.g. directly) to the deaeration means in (b). There may also be means for pasteurisation. After deaeration in (b), the deaerated liquid may be transferred or passed to a pasteurisation means, or a vessel in which the liquid (and cells) is pasteurised. Each of the means can be positioned in the order specified, in the order of the stages of the process of the first aspect.

In a preferred system, the aqueous liquid may be transferred from a fermentor to a (suitably tubular) heating system. The aqueous liquid may be (pre)heated which may in itself cause deaeration. The liquid may be heated to a temperature of from 40 to 80°, such as from 50 to 70°, such as from 55 to 65° C. The heating (or preheating stage) may therefore be part of the deaeration system. Deaeration may be further encouraged by the addition of water (the dilution technique) and/or steam (the gas replacement technique). Either or both of these may occur before (pre)heating.

After the e.g. preheating the aqueous liquid may be subjected to a further deaeration stage, for example vacuum or pressure reduction. The liquid may then be subjected to pasteurisation.

Preferred features and characteristics of one aspect of the invention are applicable to another aspect mutatis mutandis.

The invention will now be described, by way of example with reference to the following Examples, which are provided by way of illustration and are not intended to limit the scope.

Comparative Examples 1 and Examples 2 to 4

Deaeration Inside Fermentor

During some experiments that involved pasteurisation of fungal biomass (*Mortierella alpina*) some oxidation was seen. It was suspected that the explanation was the presence of the air in the fermentation broth, resulting in chemical oxidation, especially at high temperatures. Although microbial cells need air to survive and to biosynthesise PUFAs, it was decided to implement deaeration of the fermentation broth inside the fermentor, prior to pasteurisation (heat shock treatment).

Fermentation of a fungal biomass, *M. alpina*, was conducted as described previously in the art. The fermentation was conducted in a similar fashion to that as described in WO 97/36996 (see Examples). Fermentation lasted for approximately 150-200 hours. The broth was transferred from the fermentor via a small vessel (capacity 350 liters) to the pasteurisation equipment.

Trials were performed on fermentation broths from a number of similar fermentations with fermentation times of 150 to 200 hours.

In the first group of experiments, trials were performed directly on the broth while still inside the fermentor using various deaeration methods, including stopping the bubbling of air into the broth via the sparger for 2 hours prior to the end of fermentation (Example 2) and using nitrogen to replace air in the headspace above the fermentation broth (Examples 3 and 4). No deaeration methods were performed for Comparative Example 1.

The dried biomass obtained from the heatshock trials was analysed for TPC (total plate count). The results of the TPC did not deviate from the ones measured on the broth pasteurised under standard conditions. The broth, once deaerated and pasteurised, was used to isolate a microbial/single cell oil containing arachidonic acid (ARA). The arachidonic acid crude oil was recovered and analysed. The recovery system involved, after deaerating and pasteurising the broth, calcium chloride addition, filtration/washing and squeezing to form a wet cake. This wet cake was then extruded to form an extrudate, which was dried, and the resulting dried biomass subjected to extraction.

Approximately one liter of broth was found to contain about 45 to 55 grams of dried biomass, with about 30 to 35% of oil.

The following lab scale recovery process is employed. Calcium chloride addition was performed using glass laboratory vessels, with calcium chloride flakes and water. A 25% w/w solution of calcium chloride was used using $CaCl_2.2H_2O$. 24 grams of solution were added to one liter of pasteurised broth, and mixed well.

Filtration was used to simulate the membrane filter press. A one liter "Seitz" filter was used, with a Sefar Fyltis AM 25116 cloth. One liter of the broth was filtered at 0.5 to 1 bar nitrogen. It was then depressurised and 0.6 times the broth volume of washwater added, not disturbing the cake during water addition. The cake was then washed at 0.5 to 1 bar, and the cake allowed to blow dry for about one minute.

Vacuum filtration was then performed using a Pannevis labscale filtration belt filter using Pannevis cloth material. About 400 to 500 ml of broth was used, filtered to a pressure of 0.45 bara (−0.55 bar vacuum). Then, 0.6 times the volume of broth of washwater was added, and the cake washed at a pressure of 0.45 bara. The cake was then sucked dry.

The biomass was then squeezed, between plates, until no more water could be removed. This was done by using cheesecloth.

Extrusion was then performed using a meatgrinder (Victoria) extruder. The resulting granules were than dried using a fluidised bed drier, inlet temperature of 50° C., with the flow rate setting on "5" for 30 minutes. The dry matter was between 91 and 96%.

Extraction was then performed, 100 grams of dried biomass being extracted with 500 ml of hexane at ambient temperature for 60 minutes. The hexane was decanted, and the cake washed with 250 ml of fresh hexane at ambient temperature for 30 minutes. The hexane was decanted and added to the previous extracted hexane. The extract was clarified by vacuum filtration using a glass filter.

Evaporation involved flashing off the bulk hexane in the rotorvapor with a water bath temperature of 60 to 70° C. at 200 mbara for 5 to 10 minutes. The remaining hexane was also evaporated at the same temperature for 10 to 20 minutes at less then 100 mbara. To minimise oxidation the system was depressurised using nitrogen.

The resulting ARA-containing oil was then analysed for POV and AnV content as shown in Table 1 below.

TABLE 1

| Example No | Ferm. Batch | Process conditions | Pasteurisation process condition [° C.] | [sec] | POV [meq/kg] | AnV [-] |
|---|---|---|---|---|---|---|
| 1 (Comp) | B-03036 | Standard* | 100 | 10 | 16.5 | 24.3 |
| 2 | B-03050 | No air in sparger for 2 h<br>Air in headspace<br>60 rpm | 100 | 10 | 10.8 | 10.6 |
| 3 | B-03050 | 1 hour N₂<br>N₂ in headspace to 0.6 bar | 100 | 10 | 9.8 | 13.2 |
| 4 | B-03067 | No air in sparger for 2 h<br>N₂ in sparger for 2 h<br>N₂ in headspace to 0.6 bar<br>40 rpm | 100 | 10 | 8.0 | 5.5 |

*The broth was transferred by means of 1.8-2 bar head pressure in the fermenter

As can be seen from the data in Table 1, the reduction in the amount of air in the broth resulted in the POV and/or AnV improving. On the basis of these results it was thought that deaeration could achieve decreased oxidation, and improved POV and AnV values. A further trial was then set up, with a larger volume, using a separate deaerator.

Examples 5 to 14 (Separate Deaerator)

A permanent deaeration system was installed, with an "umbrella nozzle", at a working pressure of below 500 mbara. Transfer of the fermentation broth from the fermentator to the deaerator was by means of a low shear pump (monho pump).

The deaeration system, after fermentation but before pasteurisation, was installed using an APV deaeration system to mimic a parasol deaerator. The fermentor was linked to the deaerator and the broth transferred at a transfer pressure of 0.5 bar. The deaerator was connected to a vacuum pump. After passage through the deaerator biomass was sent (via a monho pump) to a holding tank, before being sent for pasteurisation using heatshock treatment equipment (also APV). The monho pump had a flow rate of 10 m³/hour and the pressure inside the deaerator was 400 mbara.

Table 2 gives the results of the trial performed using this deaeration setup. Isolation of the microbial oil and analysis was as previously described.

TABLE 2

| Example No | Fer. Batch | Process conditions | Pasteurisation process conditions [° C.] | [sec] | Deaeration pressure [mbara] | POV [meq/kg] | AnV [-] |
|---|---|---|---|---|---|---|---|
| 5 | B-031096 | No air in sparger for 1 h<br>P in headspace = 0.2 bar<br>PTF = 0.5 bar | 100 | 15 | 400 | 4.9 | 13.1 |
| 6 | B-03102 | No air in sparger for 1 h<br>P in headspace = 0.2 bar<br>PTF = 0.5 bar | 120 | 15 | 400 | 17.2 | 36.3 |
| 7 | B-03102 | No air in sparger for 1 h<br>P in headspace = 0.2 bar<br>PTF = 0.5 bar | 100 | 15 | 400 | 11.7 | 19.0 |
| 8 | B-03104 | No air in sparger for 1 h<br>P in headspace = 0.2 bar<br>PTF = 0.5 bar | 100 | 15 | 400 | 4.9 | 7.4 |
| 9 | A-03079 | No air in sparger for 1 h<br>P in headspace = 0.2 bar<br>PTF = 0.3 bar (12 m³)<br>PTF = 0.7 bar (28 m³) | 100 | 15 | 400 | 5.6 | 9.0 |
| 10 | A-03081 | No air in sparger for 1 h<br>P in headspace = 0.1 bar<br>PTF = 0.3 bar (10 m³)<br>PTF = 0.7 bar (rest of broth) | 100 | 15 | 400 | 2.9 | 6.2 |
| 11 | B-03141 | No air in sparger for 1 h<br>P in headspace = 0.1 bar<br>PTF = 0.6 bar | 100 | 15 | 400 | 7.6 | 18.4 |
| 12 | A-03092 | No air in sparger for 2 h<br>P in headspace = 0.1 bar<br>PTF = 0.6 bar | 100 | 15 | 400 | 7.8 | 17.1 |
| 13 | A-03093 | No air in sparger for 2 h<br>P in headspace = 0.1 bar<br>PTF = 0.7 bar | 100 | 15 | 400 | 9.3 | 23.1 |
| 14 | A-03095 | No air in sparger for 2 h<br>P in headspace = 0.1 bar<br>PTF = 0.7 bar | 100 | 15 | 400 | 5.2 | 7.9 |

The invention claimed is:

1. A process for producing an oil comprising at least 35% of arachidonic acid (ARA), the process comprising:
    (a) deaerating an aqueous liquid comprising microbial cells which are *Mortierella alpina* cells; and
    (b) obtaining the oil from the microbial cells,
    wherein the deaerating results in a concentration of dissolved oxygen of less than 10 ppm and wherein the aqueous liquid is a fermentation broth
    and wherein the cells are pasteurized after deaeration in (a) but before stage (b) and wherein (b) further comprises transferring the aqueous liquid to a vessel having a reduced pressure.

2. A process according to claim 1, which further comprises:
    (c) extracting, purifying or isolating the oil.

3. A process according to claim 1, wherein deaeration comprises at least one method selected from:
    a) application of vacuum or reduced pressure;
    b) mechanical deaeration/de-gassing by stirring, vibration, or use of an accelerative or g-force;
    c) viscosity change by dilution with a liquid, or by increase in temperature;
    d) change in fermentation conditions by a reduction during fermentation in at least one of airlift, air sparging, oxygen supply, air supply, or stirring rate;
    e) pH change;
    f) filtration;
    g) gas displacement, with an inert gas;
    h) chemical deaeration; and
    i) time, wherein the aqueous liquid is allowed to rest under conditions such that oxygen or air diffuses out of the liquid.

4. A process according to claim 1 wherein the deaeration is effected by reduced stirring and/or gas displacement.

5. A process according to claim 4 wherein gas displacement is performed using a gas comprising either no oxygen or oxygen at a concentration level below atmospheric air.

6. A process according to claim 5 wherein the gas is, or comprises, nitrogen.

7. A process according to claim 1 wherein deaeration comprises subjecting the aqueous liquid to reduced pressure.

8. A process according to claim 7, wherein said reduced pressure is a pressure of no more than 800 mbara.

9. A process according to claim 7, wherein the aqueous liquid is deaerated using a vacuum or degassing pump, a parasol deaerator or an umbrella nozzle.

10. A process according to claim 1, wherein deaeration results in a concentration of dissolved oxygen of less than 5 ppm.

11. A process according to claim 10, wherein deaeration results in a concentration of dissolved oxygen of less than 2 ppm.

12. A process according to claim 1, wherein the process comprises subjecting the deaerated aqueous liquid to a temperature between 60-150° C.

13. A process according to claim 12, wherein the process comprises subjecting the deaerated aqueous liquid to a temperature between 110-150° C.

14. A process according to claim 1, wherein the cells are heated or pasteurised at a temperature 80-150° C.

15. A process according to claim 14, wherein the cells are heated or pasteurized at a temperature between 110-150° C.

16. A process according to claim 1, wherein the oil comprises at least 40% of ARA.

* * * * *